United States Patent [19]

Yonan

[11] 4,076,707
[45] Feb. 28, 1978

[54] N-(2-HEXAMETHYLENIMINOETHYL)-5H-DIBENZ[b,f]-AZEPINE-5-CARBOXAMIDES AND QUATERNARY AMMONIUM DERIVATIVES THEREOF

[75] Inventor: Peter K. Yonan, Morton Grove, Ill.

[73] Assignee: G. D. Searle & Co., Chicago, Ill.

[21] Appl. No.: 689,446

[22] Filed: May 24, 1976

Related U.S. Application Data

[63] Continuation-in-part of Ser. No. 492,454, Jul. 29, 1974, abandoned.

[51] Int. Cl.$^2$ .................. G07D 223/26; A61K 31/55
[52] U.S. Cl. ................................. 260/239 D; 424/244
[58] Field of Search ..................................... 260/239 D

[56] References Cited

U.S. PATENT DOCUMENTS

| 2,666,051 | 1/1959 | Hafliger et al. | 260/239 D |
| 2,965,638 | 12/1960 | Schindler et al. | 260/239 D |

OTHER PUBLICATIONS

A. Burger, (Ed.), "Medicinal Chemistry", 2nd Ed., pp. 42 & 497 (1960).

*Primary Examiner*—Donald G. Daus
*Assistant Examiner*—D. B. Springer
*Attorney, Agent, or Firm*—John J. McDonnell

[57] ABSTRACT

N-(hexamethyleniminoalkyl)-5H-dibenz[b,f]-azepine-5-carboxamides having anti-arrhythmic activity are described herein. The subject compounds can be prepared by reacting a 5H-dibenz[b,f]azepine-5-carbonyl chloride with the appropriate hexamethyleniminoalkylamine.

6 Claims, No Drawings

N-(2-HEXAMETHYLENIMINOETHYL)-5H-DIBENZ[b,f]-AZEPINE-5-CARBOXAMIDES AND QUATERNARY AMMONIUM DERIVATIVES THEREOF

The present application is a continuation-in-part of application Ser. No. 492,454, filed July 29, 1974, now abandoned.

The present invention relates to a group of N-(hexamethyleniminoalkyl)-5H-dibenz[b,f]azepine-5-carboxamides. More particularly, the present invention relates to a group of compounds having the general formula

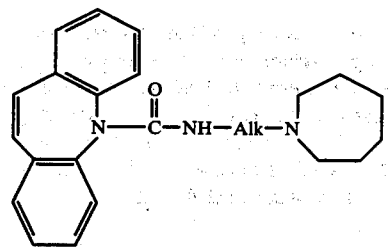

wherein Alk is lower alkylene separating the nitrogen atoms attached thereto by at least 2 carbon atoms. Additionally contemplated by the present invention are those compounds wherein one of the benzene rings of the dibenz[b,f]azepine structure is further substituted by a halogen, lower alkyl or methoxy group; and those compounds wherein the carboxamide nitrogen is additionally substituted by a lower alkyl group.

The lower alkyl groups referred to above contain 1 to 6 carbon atoms and are exemplified by methyl, ethyl, propyl, isopropyl and the like. The lower alkylene groups referred to above contain 2 to 6 carbon atoms and can be exemplified by groups such as ethylene, propylene, trimethylene and 1,4-pentylene. The halogen atoms include fluorine, chlorine, bromine and iodine.

Equivalent to the above amines for the purposes of this invention are the pharmaceutically acceptable acid addition and quaternary ammonium salts thereof. Such acid addition salts can be derived from a variety of organic and inorganic acids such as sulfuric, phosphoric, hydrochloric, hydrobromic, hydriodic, sulfamic, citric, lactic, maleic, succinic, tartaric, cinnamic, acetic, benzoic, gluconic, ascorbic, and related acids. Similarly, the quaternary ammonium salts can be derived from a variety of organic esters of sulfuric, hydrohalic and aromatic sulfonic acids and particularly preferred are the quaternary ammonium salts derived from lower alkyl halides wherein the lower alkyl group contains up to six carbon atoms. Among such preferred lower alkyl halides are methyl chloride, bromide and iodide; ethyl chloride, propyl chloride, butyl chloride, isobutyl chloride. Among the other esters which can be used to prepare quaternary ammonium salts are benzyl chloride and bromide, phenethyl bromide, naphthylmethyl chloride, dimethyl sulfate, methyl benzenesulfonate, ethyl toluenesulfonate, ethylene chlorohydrin, propylene chlorohydrin, allyl bromide, methallyl bromide and crotyl bromide.

The compounds of this invention are useful because of their pharmacological properties. In particular, they possess activity as anti-arrhythmic agents. Thus, they bring about a return to normal heart rhythm in animals in which the heart rhythm has become irregular.

The anti-arrhythmic utility of the instant compounds is evident from the results of a standardized test for their capacity to slow the ventricular tachycardia induced by aconitine in the isolated rabbit heart. The procedure is essentially that described by Lucchesi [J. Pharmacol. Exp. Therap., 137, 291 (1962)], modified in certain particulars as follows: Hearts are obtained from adult albino rabbits of either sex and perfused in apparatus modeled after that devised by Anderson and Craver [J. Pharmacol. Exp. Therap., 93, 135 (1948)]. The composition of the perfusion solution is the same as Lucchesi's, but the volume is increased to 200 ml. and the temperature lowered to 28° C. Aconitine (ordinarily as the nitrate) is administered as soon as the heart beat is regular and the EKG pattern normal, the dose being so selected as to at least double the rate. Typically, 0.05 ml. of 0.1% aconitine nitrate in physiological saline is injected. EKG's are recorded at five minute intervals after onset of ventricular tachycardia until two successive readings show stabilization of the rate. Perfusate collected during this time is discarded and replaced with fresh solution q.s. 200 ml. Promptly following stabilization, 2 mg. of compound dissolved or suspended in 1 ml. of physiological saline is mixed with the perfusion solution. Ten minutes later a like amount is introduced, followed after a further 10 minutes by double the first amount. Final concentration of compound in the perfusion solution is thus 40 mg. per liter. Recording of EKG's is continued at five minute intervals throughout this time and for ten minutes thereafter. A compound is considered anti-arrhythmic if, at any time during the 30 minutes immediately following initial administration in at least half of a minimum of two tests, it reduces by 50% or more the rate recorded ten minutes after onset of tachycardia. Among the compounds of this invention which have been found particularly active in this test are the representative compounds N-(2-hexamethyleniminoethyl)-5H-dibenz[b,f]azepine-5-carboxamide and N-(3-hexamethyleniminopropyl)-5H-dibenz[b,f]azepine-5-carboxamide.

A further test demonstrating the anti-arrhythmic utility of the present compounds is as follows:

Male mongrel dogs are connected to a physiograph to follow heart and blood action. At the onset of the testing, an initial dose of 40 mcg./kg. ouabain is administered intravenously in a saline solution. This is followed 30 minutes later by a dose of 20 mcg./kg. of ouabain and, at 15 minute intervals, by a dose of 10 mcg./kg. of ouabain until ventricular arrhythmia occurs and persists for twenty minutes. Then, a saline solution of test compound is administered at a dose of 5 mg./kg. If the heart action does not become normal, additional test compound is administered at a dose of 5 mg./kg. at 15 minute intervals until heart action becomes normal or until the total dose of test compound administered is 20 mg./kg. The procedure is run in two dogs. A compound is considered anti-arrhythmic if it causes a return to normal heart action for a period of 15 minutes or more in half or more of the dogs tested at a dose of 20 mg./kg. or less. Compounds which show activity in this test are N-(2-hexamethyleniminoethyl)-5H-dibenz[b,f]azepine-5-carboxamide, N-(3-hexamethyleniminopropyl)-5H-dibenz[b,f]azepine-5-carboxamide, and N-(2-hexamethyleniminoethyl)-5H-dibenz[b,f]azepine-5-carboxamide methiodide.

The compounds of the present invention can be conveniently prepared by contacting a compound of the formula

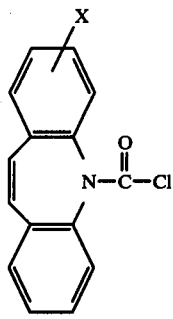

with the appropriate hexamethyleniminoalkylamine of the formula

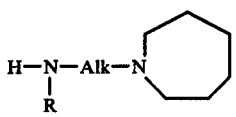

wherein Alk is defined as before; X is hydrogen, halogen, lower alkyl or methoxy; and R is hydrogen or lower alkyl. Depending on the nature of the reactants, it is possible to carry out this reaction in the presence or absence of a solvent. The use of an inert solvent is, however, generally preferred. An especially useful solvent is chloroform, while other possible solvents would include aromatic hydrocarbons such as benzene and toluene, halogenated hydrocarbons such as methylene chloride and carbon tetrachloride, ketones such as acetone and 2-butanone and ethers such as ethyl ether, tetrahydrofuran and dioxane. The reaction proceeds in the presence of an acid acceptor. Excess amine reactant above can serve as the acid acceptor or, alternatively, a separate acid acceptor, for example a tertiary amine (e.g., N-methyl-morpholine, trimethylamine or, preferably triethylamine) can be added to the reaction mixture. Time and temperature are not critical factors. Reaction temperatures can vary from room temperature to reflux and typical times being in the range of 1-5 hours.

The invention will appear more fully from the examples which follow. These examples are given by way of illustration only and are not to be construed as limiting the invention either in spirit or in scope as many modifications both in materials and methods will be apparent to those skilled in the art. In these examples, temperatures are given in degrees centigrate (° C.) and quantities of materials are expressed in parts by weight unless otherwise specified. The relationship between parts by weight and parts by volume is the same as that existing between grams and milliliters.

EXAMPLE 1

A solution of 6.0 parts of 5H-dibenz[b,f]-azepine-5-carbonyl chloride in 70 parts of chloroform is added dropwise over a 30 minute period to a hot solution of 4.0 parts of 2-hexamethyleniminoethylamine in 14.5 parts of triethylamine and 210 parts of chloroform. The mixture is refluxed for an additional 90 minutes and cooled. It is then treated with decolorizing carbon, dried over anhydrous calcium sulfate and evaporated to dryness. The solid thus obtained is crystallized from a mixture of chloroform and n-hexane to afford N-(2-hexamethyleniminoethyl)-5H-dibenz[b,f]-azepine-5-carboxamide, melting at about 157°-159° C. That compound can be represented by the following structural formula

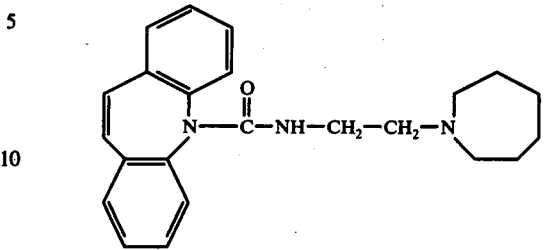

Substitution of an equivalent quantity of 3-hexamethyleniminopropylamine for the 2-hexamethyleniminoethylamine used above and substantial repetition of the foregoing procedure affords N-(3-hexamethyleniminopropyl)-5H-dibenz[b,f]azepine-5-carboxamide, melting at about 92°-94° C. That compound can be represented by the following structural formula

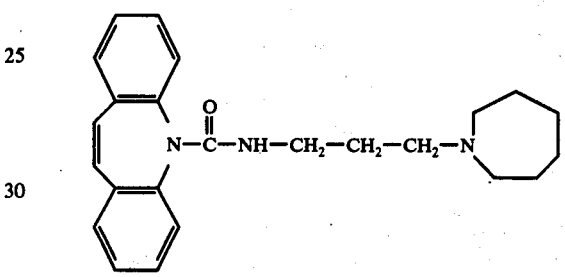

EXAMPLE 2

3.0 Parts of N-(2-hexamethyleniminoethyl)-5H-dibenz[b,f]azepine-5-carboxamide is dissolved in 54.0 parts of methyl iodide, placed in a pressure flask, and heated at 65° C. for 2 hours. Ethyl ether is added to the reaction mixture, and the solid is then separated by filtration and crystallized from a mixture of ethanol and ethyl ether. The product thus obtained is N-(2-hexamethyleniminoethyl)-5H-dibenz[b,f]azepine-5-carboxamide methiodide, melting at about 239°-241° C. That product can be represented by the following structural formula

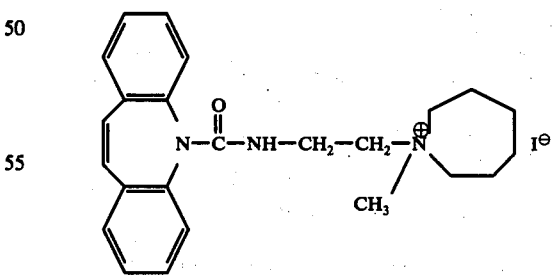

When the above procedure is repeated using an equivalent quantity of N-(3-hexamethyleniminopropyl)-5H-dibenz[b,f]azepine-5-carboxamide for the N-(2-hexamethyleniminoethyl)-5H-dibenz[b,f]azepine-5-carboxamide used above, there is obtained N-(3-hexamethyleniminopropyl)-5H-dibenz[b,f]azepine-5-carboxamide methiodide. That product melts at about 219°-221° C. after crystallization from a mixture of ethanol and 2-propanol. That compound can be represented by the following structural formula

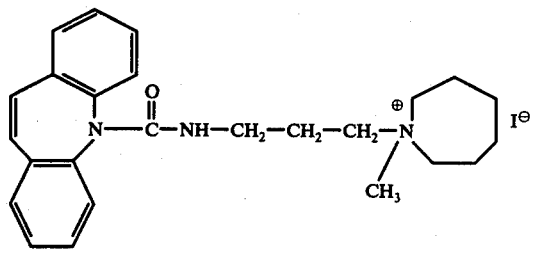

EXAMPLE 3

12.5 Parts of N-(2-hexamethyleniminoethyl)-5H-dibenz[b,f]azepine-5-carboxamide is dissolved in 119 parts of ethanol and an excess of hydrogen chloride in 2-propanol is added. The mixture is heated and 355 parts of ethyl ether is added. The crystals which form upon cooling are separated and recrystallized from a mixture of ethanol and ethyl ether to give N-(2-hexamethyleniminoethyl)-5H-dibenz[b,f]azepine-5-carboxamide hydrochloride, melting at about 207°–209° C. That compound can be represented by the following structural formula

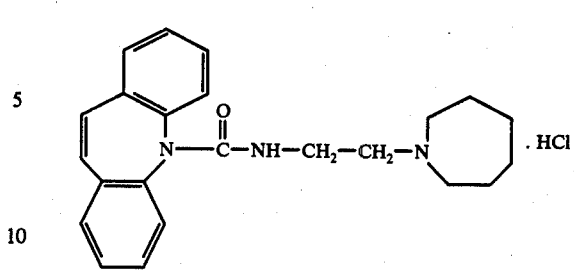

What is claimed is:
1. A member selected from the group consisting of compounds of the formula

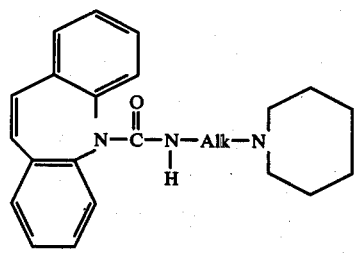

wherein Alk is lower alkylene separating the nitrogen atoms attached thereto by at least 2 carbon atoms; and the pharmaceutically acceptable acid addition and lower alkyl halide having 1 to 6 carbon atoms quaternary ammonium salts thereof.

2. A compound according to claim 1 which is N-(2-hexamethyleniminoethyl)-5H-dibenz[b,f]azepine-5-carboxamide.

3. A compound according to claim 1 which is N-(3-hexamethyleniminopropyl)-5H-dibenz[b,f]azepine-5-carboxamide.

4. A compound according to claim 1 which is N-(2-hexamethyleniminoethyl)-5H-dibenz[b,f]azepine-5-carboxamide methiodide.

5. A compound according to claim 1 which is N-(3-hexamethyleniminopropyl)-5H-dibenz[b,f]azepine-5-carboxamide methiodide.

6. A compound according to claim 1 which is N-(2-hexamethyleniminoethyl)-5H-dibenz[b,f]azepine-5-carboxamide hydrochloride.

* * * * *